United States Patent [19]

Kahan et al.

[11] Patent Number: 4,668,504

[45] Date of Patent: May 26, 1987

[54] USE OF SUBSTITUTED PROPENOATES TO PREVENT NEPHROTOXICITY OF CERTAIN ANTIBIOTICS

[75] Inventors: Frederick M. Kahan, Scotch Plains; Helmut Kropp, Kenilworth, both of N.J.

[73] Assignee: Merck & Co., Inc., Rahway, N.J.

[21] Appl. No.: 856,437

[22] Filed: Apr. 22, 1986

Related U.S. Application Data

[63] Continuation of Ser. No. 474,863, Mar. 14, 1983, abandoned, which is a continuation of Ser. No. 187,931, Sep. 17, 1980, abandoned, which is a continuation-in-part of Ser. No. 90,793, Nov. 2, 1970, abandoned.

[51] Int. Cl.$^4$ .............................................. A61V 27/00
[52] U.S. Cl. ...................................................... 424/10
[58] Field of Search ............................................ 424/10

[56] References Cited

U.S. PATENT DOCUMENTS 4,539,208  9/1985  Kahan et al. ...................... 514/195

Primary Examiner—Stanley J. Friedman
Attorney, Agent, or Firm—Robert J. North; Hesna J. Pfeiffer

[57] ABSTRACT

Antibiotics to prevent nephrotoxicity.

21 Claims, No Drawings

USE OF SUBSTITUTED PROPENOATES TO PREVENT NEPHROTOXICITY OF CERTAIN ANTIBIOTICS

This is a continuation of application Ser. No. 474,863, filed Mar. 14, 1983, now abandoned, which is a continuation of application Ser. No. 187,931, filed Sept. 17, 1980, now abandoned which case is a continuation-in-part of copending U.S. Ser. No. 090,793, filed Nov. 2, 1979, now abandoned.

BACKGROUND OF THE INVENTION

The use of the β-lactam antibiotic cephaloridine in man is associated with a significant incidence of nephrotoxicity. The nephrotoxic potential of this and other antibiotics can be duplicated in laboratory studies in the rabbit wherein single large doses of the antibiotic are found to produce within 48 hours an elevation of the level in blood of nitrogenous substances normally excreted by the kidney. Subsequent microscopic examination of the kidneys reveals renal tubular epithelial necrosis. In this laboratory model, the new β-lactam antibiotic N-formimidoyl thienamycin has also been shown nephrotoxic at dose rates comparable to those used with cephaloridine. The nephrotoxic activity of both antibiotics can be prevented by co-administration of a 3-substituted propenoate of the following Formula I, below. An additional group of compounds useful is described by Formula II, also below. The compounds of Formula I:

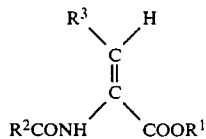

wherein $R^2$ and $R^3$ are hydrocarbon radicals in the range respectively of 3–10 and 1–15 carbon atoms. In either of these hydrocarbon radicals $R^2$ and $R^3$, up to 6 hydrogens may be replaced by halogens, or a non-terminal methylene may be replaced by oxygen or sulfur, including oxidized forms of the latter A terminal hydrogen in $R^3$ can also be replaced by a hydroxyl or thiol group, which may be acylated, such as with an alkanoyl acid of 1–8 carbon atoms, or carbamoylated, including alkyl and dialkyl carbamate derivatives; or the hydrogen can be replaced by an amino group, which may be derivatized as in an acylamino, ureido, amidino, guanidino, or alkyl or substituted alkyl amino group, including quaternary nitrogen groupings; or, alternatively, there may be replacement by acid groups such as carboxylic, phosphonic or sulfonic acid groups or esters or amides thereof, as well as cyano; or combinations thereof, such as a terminal amino acid grouping.

$R^2$ is preferably a branched alkyl or cycloalkyl radical ($C_{3-10}$), with a limitation that the carbon adjacent to the carbonyl cannot be tertiary. $R^1$ is hydrogen, lower-alkyl ) or dialkylaminoalkyl (e.g., $-CH_2CH_2N(C_2H_5)_2$, $-CH_2CH(CH_3)N(C_3H_2)$.

The compounds of Formula I are not novel to this invention, but are disclosed and claimed in U.S. Ser. No. 927,212, filed July 24, 1978, and now abandoned, and its continuation-in-part application, U.S. Ser. No. 050,233, filed June 22, 1979, now abandoned. It is presently believed that all compounds within the scope of this Formula possess the ability to prevent nephrotoxicity. One compound in particular has been shown to possess this property; this compound is Z-2-(2,2-dimethylcyclopropane carboxamido)-2-octenoic acid. Particularly preferred compounds, in addition to the latter, are the following: Z-2-(2,2-dimethylcyclopropane carboxamido)-2-butenoic acid; Z-2-(2,2-dimethylcyclopropane carboxamido)-2-pentenoic acid; Z-2-(2,2-dimethylcyclopropane carboxamido)-2-hexenoic acid; and Z-2-(2,2-dimethylcyclopropane carboxamido)-8-trimethylammonium-2-octenoic acid.

The compounds of Formula I have previously been taught as useful as pharmaceutical compositions in combination with the thienamycins, but not with cephaloridine. The combination is disclosed and claimed in U.S. Ser. No. 927,213, filed July 24, 1978, and now abandoned, and in its continuation-in-part application, U.S. Ser. No. 050,232, filed June 22, 1979, and now abandoned.

Within the general structure of Formula I, the following sub-groups of compounds are valuable:

Within the definition of $R^2$, the following sub-groups are included:

$$-R^4 \qquad \text{I A}$$

wherein $R^4$ is a straight, branched, or cyclic hydrocarbon radical of 3–10 carbon atoms which may be substituted as specified above in the definition of $R^2$;

$$-R^5R^6 \qquad \text{I B}$$

wherein $R^5$ is cycloalkyl of 3–6 carbon atoms and $R^6$ is either 1 or 2 alkyl substituents which may be joined to form another ring on the cycloalkyl group, or $R^5$ and $R^6$ may be substituted as specified above in the definition of $R^2$;

$$-R^7R^8 \qquad \text{I C}$$

wherein $R^7$ is an alkylene group of 1–3 carbon atoms and $R_8$ is cycloalkyl of 3–6 carbon atoms which may be substituted as specified above in the definitions of $R^2$ and $R^3$.

The following compounds within this Formula are included in this invention.

I A: Z-2-isovaleramido-2-pentenoic acid; methyl Z-2-isovaleramido-2-butenoate; Z-2-isovaleramido-2-butenoic acid; Z-2-benzamido-2-butenoic acid; Z-2-(3,5,5-trimethylhexanamido)-2-butenoic acid; Z-2-cyclobutanecarboxamido-2-butenoic acid; Z-2-cyclopropanecarboxamido-2-butenoic acid; Z-2-cyclopropanecarboxamido-2-pentenoic acid; Z-2-(3-methylvaleramido)-2-butenoic acid; Z-2-cycloheptanecarboxamido-2-butenoic acid; Z-2-nonanamido-2butenoic acid; Z-2-cyclohexanecarboxamido-2-butenoic acid; Z-2-(4-methylvaleramido)-2-butenoic acid; Z-2-t-butylacetamido-2-butenoic acid; Z-2-octanamido-2-butenoic acid; Z-2-butyramido-2-butenoic acid; Z-2-valeramido-2-butenoic acid; Z-2-valeramido-2-pentenoic acid; Z-2-cyclopentanecarboxamido-2-butenoic acid; Z-2-(6-methylheptanamido)-2-butenoic acid; Z-2-hexanamido-2-butenoic acid; Z-2-(3,7-dimethyloctanamido)-2-butenoic acid; Z-2-(3,7-dimethyl-6-octenamido)-2-butenoic acid; Z-2-(5-chlorovaleramido)-2-butenoic acid; Z-2-(3-chlorobenzoylamido)-2-butenoic acid;

Z-2-(2-chlorobenzamido)-2-butenoic acid; Z-2-(6-bromohexanamido)-2-butenoic acid; Z-2-(3,3-dimethylpropenamido)-2-butenoic acid; Z-2-benzamido-2-cinnamic acid; Z-2-benzamido-2-pentenoic acid; Z-2-benzamido-5-methoxy-2-pentenoic acid; Z-2-benzamido-2-hexenedioic acid; Z-2-isovaleramido-2-octenoic acid; Z-2-isovaleramido-2-cinnamic acid; Z-2-isovaleramido-2-hexenedioic acid; Z-2-cyclopropanecarboxamido-2-cinnamic acid; Z-2-cyclopropanecarboxamido-2-hexenedioic acid; Z-2-(5-methoxy-3-methylvaleramido)-2-butenoic acid; Z-2-ethylthioacetamido-2-butenoic acid; Z-2-(2,2-dichlorocyclopropanecarboxamido)-2-butenoic acid; Z-2-(2-ethylhexanamido)-2-butenoic acid; Z-2-di-n-propylacetamido-2-butenoic acid;

I B: Z-2-(2,2-dimethylcyclopropanecarboxamido)-2-butenoic acid; (+)-Z-2-(2,2-dimethylcyclopropanecarboxamido)-2-butenoic acid; Z-2-(2,2-dimethylcyclopropanecarboxamido)-2-pentenoic acid; Z-2-(2,2-dimethylcyclopropanecarboxamido)-2-octenoic acid; Z-2-(2,2-dimethylcyclopropanecarboxamido)-2-hexenoic acid; Z-2-(2,2-dimethylcyclopropanecarboxamido)-2-cinnamic acid; Z-2-(2,2-dimethylcyclopropanecarboxamido)-5-methoxy-2-pentenoic acid; Z-2-(2,2-dimethylcyclopropanecarboxamido)-4,4,4-trifluoro-2-butenoic acid; Z-2-(2,2-dimethylcyclopropanecarboxamido)-3-(2-chlorophenyl)propenoic acid; Z-2-(2,2-dimethylcyclopropanecarboxamido)-2hexenedioic acid; Z-2-(2-ethylcyclopropanecarboxamido)-2-butenoic acid; Z-2-(2,2-diethylcyclopropanecarboxamido)-2-butenoic acid; Z-2-(2,2-diethylcyclopropanecarboxamido)-2-pentenoic acid; Z-2-(2-isopropyl-2-methylcyclopropanecarboxamido)-2-butenoic acid; Z-2-(2-methylcyclohexanecarboxamido)-2-butenoic acid; Z-5-cyano-2-(2,2-dimethylcyclopropanecarboxamido)-2-pentenoic acid; Z-5-(N,N-dimethylcarbamoyl)-2-(2,2-dimethylcyclopropanecarboxamido)-2-pentenoic acid; Z-2-(2,2-dimethylcyclopropanecarboxamido)-5-methanesulfonyl-2-pentenoic acid; Z-2-(2,2-dimethylcyclopropanecarboxamido)-5-ethoxycarbonyl-2-pentenoic acid; Z-2-(2-methylcyclopropanecarboxamido)-2-butenoic acid; methyl Z-2-(2,2-dimethylcyclopropanecarboxamido)-2-butenoate; ethyl Z-2-(2,2-dimethylcyclopropanecarboxamido)-2-butenoate; 2-dimethylaminoethyl ester of Z-2-(2,2-dimethylcyclopropanecarboxamido)-2-butenoic acid; 3-diethylaminoproipyl ester of Z-2-(2,2-dimethylcyclopropanecarboxamido)-2-pentenoic acid; Z-2-(2,3-dimethylcyclopropanecarboxamido)-2-butenoic acid; Z-2-(3,3-dimethylcyclobutanecarboxamido)-2-butenoic acid; Z-2-(2-spirocyclopentanecarboxamido)-2-butenoic acid; Z-2-(2-t-butyl-3,3-dimethylcyclopropanecarboxamido)-2-butenoic acid; Z-2-(2,2-dimethylcyclopropanecarboxamido)-4-methyl-2-pentenoic acid; Z-2-(2-t-butylcyclopropanecarboxamido)-2-butenoic acid; Z-2-(2-phenylcyclopropanecarboxamido)-2-butenoic acid; Z-3-cyclohexyl-2-(2,2-dimethylcyclopropanecarboxamido)propenoic acid; Z-5-carboxy-5-(2,2-dimethylcyclopropanecarboxamido)-4-pentenamidine; Z-5-dimethyl amino-2-(2,2-dimethylcyclopropanecarboxamido)-2-pentenoic acid; Z-3-cyclopropyl-2-(2,2-dimethylcyclopropanecarboxamido)propenoic acid; Z-2-(2,2-dimethylcyclopropanecarboxamido)-2,5-hexadienoic acid; Z-2-(2,2-dimethylcyclopropanecarboxamido)-4-phenyl-2-butenoic acid; Z-2-(2,2-dimethylcyclopropanecarboxamido)-6-mercapto-2-hexenoic acid; Z-2-(2,2-dimethylcyclopropanecarboxamido)-5-methylthio-2-pentenoic acid; Z-2-(2,2-dimethylcyclopropanecarboxamido)-5-phosphono-2-pentenoic acid; Z-2-(2,2-dimethylcyclopropanecarboxamido)-2-heptenoic acid; Z-2-(2,2-dimethylcyclopropanecarboxamido)-5-phenyl-2-pentenoic acid; Z-2-(2,2-dimethylcyclopropanecarboxamido)-2-nonenoic acid; Z-2-(2,2-dimethylcyclopropanecarboxamido)-2-decenoic acid; Z-2-(2,2-dimethylcyclopropanecarboxamido)-2-tridecenoic acid; Z-2-(2,2-dimethylcyclopropanecarboxamido)-6-methoxy-2-hexenoic acid; Z-2-(2,2-dimethylcyclopropanecarboxamido)-6-methyl-2-heptenoic acid; Z-4-cyclohexyl-2-(2,2-dimethylcyclopropanecarboxamido)-2-butenoic acid;

I C: Z-2-cyclobutylacetamido-2-butenoic acid; Z-2-cyclopentylacetamido-2-butenoic acid; Z-2-cyclohexylacetamido-2-butenoic acid; Z-2-(4-cyclohexylbutyramido)-2-butenoic acid; Z-2-cyclopropylacetamido-2-butenoic acid; Z-2-cyclopropylacetamido-2-pentenoic acid; Z-2-(3-cyclopentylpropionamido)-2-butenoic acid; Z-2-(3-cyclohexylpropionamido)-2-butenoic acid; Z-2-(4-(2-thienyl)-butyramido)-2butenoic acid; Z-2-(4-phenylbutyramido)-2-butenoic acid; Z-2-(D,L-α-lipoamido)-2-pentenoic acid; Z-2-(D,L-α-lipoamido)-2-cinnamic acid; Z-2-(3-(2-tetrahydrofuryl)-propionamido)-2-butenoic acid.

Particularly preferred substituents within the definition of $R^2$ above include the 2,2-dimethylcyclopropyl and the 2,2-dichlorocyclopropyl groups.

Within the definition of $R^3$, particularly preferred groups of compounds include n-alkyl (1-9 carbons) and n-alkyl (1-9 carbons), having a terminal substituent which is a quaternary nitrogen, amine derivative, or amino acid derived group.

By the term "quaternary nitrogen" is meant a tetrasubstituted or heteroaromatic nitrogen which is positively charged. An ammonium moiety, substituted groups having 1-7 carbon atoms, which can be the same or different, is signified.

By the term "amino derivative" is meant a group such as amino, acylamino, ureido, amidino, guanidino and alkyl derivatives thereof.

By the term "amino acid derived group" is meant a moiety such as cysteinyl ($-SCH_2CH(NH_2)COOH$) or sarcosyl ($-N(CH_3)_{CH_2}COOH$) in which a hydrogen joined to O, N or S of known amino acids is replaced.

Particularly preferred compounds from the most preferred groups of substituents of $R^2$ and R are those wherein $R^2$ is 2,2-dimethylcyclopropyl or 2,2-dichlorocyclopropyl, and $R^3$ is a hydrocarbon chain of 1 to 3 carbon atoms without a terminal substituent, or 3 to 7 carbon atoms having a terminal substituent which is trimethylammonium, amidino, guanidino, 2-amino-2-carboxyethylthio, or ureido.

An additional group of propenoate compounds similar in structure to those of Formula I, have the following formula:

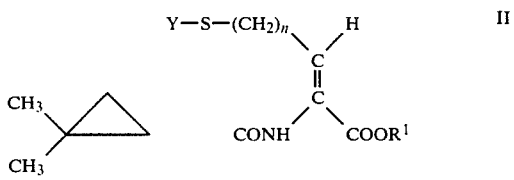

II wherein n is an integer from 3 to 5 and Y is a heterocyclic or phenyl group which may be substituted or unsubstituted. By the term heterocyclic is meant pyridyl, pyrimidinyl, tetrazolyl, imidazoyl, thiadiazolyl and the like. These rings, and the phenyl ring can be unsubstituted or substituted with hydroxyl, oxo, carboxyl, or methyl. Desirable Y groups include 2-pyridyl, 4-pyridyl, 2-pyridyl-3-hydroxyl, 2-pyridyl-3-carboxyl, 2-pyridyl-4-carboxyl, 2-carboxylphenyl, 1-methyl-1,2,3,4-tertazo-5-yl, 4-carboxy-6-hydroxy-2-pyrimidinyl, and others.

The compounds of Formula II are claimed in a copending U.S. application, U.S. Ser. No. 285,161, case 16544IA, now U.S. Pat. No. 4,406,902, Ashton et al, filed concurrently herewith.

Although these compounds of Formulas I and II, when $R^1$ is H, are described and named as the free acids, it will be apparent to one skilled in the art that various pharmaceutically acceptable derivatives such as alkali and alkaline earth metal, ammonium, or amine salts, or the like can be employed as equivalents thereto. Salts such as the sodium, potassium, calcium, magnesium, or tetramethylammonium salts are suitable.

The benefit of the 3-substituted propenoates is best appreciated when they are co-administered with the antibiotic, to human or animals in need of antibiotic therapy.

The combination of the 3-substituted propenoate and the antibiotic can be in the form of a pharmaceutical composition containing the two compounds in a pharmaceutically acceptable carrier. The two can be employed in amounts so that the weight ratio of the antibiotic to propenoate is 1 to 0.1–3 and preferably 1 to 0.5–2.0.

The components can also be separately administered. For instance, the antibiotic can be administered intramuscularly or intravenously in amounts of 2–150 mg/kg/day, preferably 5–75 mg/kg/day, in divided dosage forms, e.g., two to four times a day. The propenoate can be separately administered, orally, intramuscularly, or IV, in amounts of 1–300 mg/kg/day, or preferably 2.5–150 mg/kg/day, The amounts of the two components administered during one day ideally are within the ratio limits denoted above.

The components, whether administered separately or together are employed in pharmaceutically acceptable carriers such as conventional vehicles adapted for oral adminstration such as capsules, tablets, or liquid solutions or suspensions. The components separately or together, can also be dissolved in a vehicle adapted for administration by injection. Suitable formulations for oral use, may include diluents, granulating agents, preservatives, binders, flavoring agents, and coating agents. The example of an oral use composition in the combination of active ingredients, or the acid component alone, intermixed in the dry pulverulent state with gelatin, starch, magnesium stearate, and alginic acid, and pressed into a tablet.

As noted above, the presently known preferred method is parenteral administration of the antibiotic and either co-parenteral administration or oral administration of the propenoate compound.

EXAMPLES ILLUSTRATING CHEMICAL PREPARATIONS

The propenoate compounds are novel compounds claimed in a copending application. These compounds are made by condensing directly the appropriate 2-keto acid and amide:

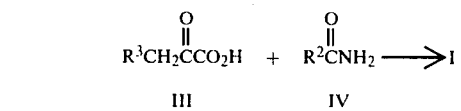

wherein $R^2$ and $R^3$ are as defined. The general reaction conditions involve mixing approximately 1–4:1 parts of the acid to the amide in an inert solvent such as toluene or methyl isovalerate and heating at reflux with azeotropic removal of water for from 3–48 hours, preferably 5–24 hours. The solution when cooled normally yields the product in crystalline form, but the product can also be isolated using a base extraction process. The product can be recrystallized by using generally known techniques. An optional modification of this procedure requires an additional small amount of p-toluenesulfonic acid as catalyst during the reaction.

Another route to these compounds uses an α-amino acid, t-butyl ester in reaction with an acid chloride:

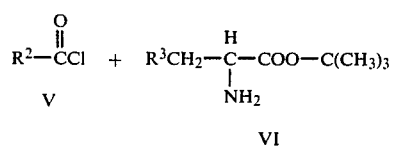

This reaction takes place in the presence of base, such as triethylamine, in a solvent such as methylene chloride. The resulting N-acylated product (VII) is then oxidized by treatment with t-butyl hypochlorite followed by addition of sodium methoxide. This yields the 2-methoxy derivative (VIII) and/or its elimination product, the α,β-unsaturated ester (IX). Further treatment with anhydrous hydrochloric acid converts either VIII or IX (or the mixture of both) to the desired α,β-unsaturated free acid (II).

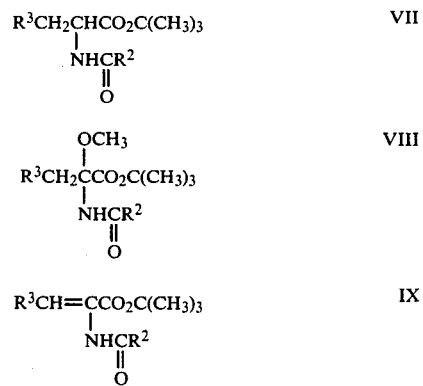

Some compounds wherein $R^3$ has a terminal substituent which is an amino, quaternary nitrogen, thiol or carboxyl, derivative; or the compounds of Formula II can be made most conveniently from an intermediate having a bromo substituent instead of the desired terminal substituent, followed by condensation with the desired thiol, amino, acid, or the like.

Another route for preparing compounds when $R^3$ is a terminally substituted thio derivative (also compounds of Formula II) utilizes a chloro-keto ester intermediate

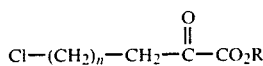

in reaction with the desired amide,

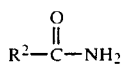

in toluene at reflux in the presence of a catalytic amount of p-toluenesulfonic acid. The resulting intermediate is hydrolyzed to the acid; the chloro group is then displaced in reaction with the appropriate mercapton. This reaction is valuable since it permits use of the chiral amide IV, thereby preparing a functionalized side chain. In addition, the mixture of Z+E isomers prepared after the mercapton condensation can be directly resolved into the Z form by adding acid to a pH about 3, and heating to about 90° C. for 30 minutes. Only the Z form remains, and recovery is simple and straight forward.

More detail about preparation of the compounds is found in the following examples.

EXAMPLE 1

Z-2-(2,2-Dimethylcyclopropanecarboxamido)-2-pentenoic acid

A solution of 1.74 g (15 mmole) of 2-ketovaleric acid and 1.13 g (10 mmole) of 2,2-dimethylcyclopropanecarboxamide in 20 ml of toluene was refluxed with stirring with collection of $H_2O$ in a small Dean-Stark trap. After 20 hrs. the solution was cooled and treated with a gentle stream of $N_2$. Before much of the solvent had evaporated, crystallization was induced by scratching. After standing, the solid was collected on a filter and washed with toluene and some $Et_2O$. Yield of white crystals=0.63 g (30%), mp 154.5°–155.5° (slight prelim. softening). Tlc (4:1 toluene-AcOH) showed only an extremely faint trace of the other isomer. NMR was consistent with the Z-configuration.

| Anal. ($C_{11}H_{17}NO_3$) | Calcd. | Found |
| --- | --- | --- |
| C | 62.53 | 62.86 |
| H | 8.11 | 8.27 |
| N | 6.63 | 6.75 |

EXAMPLE 2

Z-2-(2,2-Dimethylcyclopropanecarboxamido)-2-butenoic acid 1.53 g (15 mmoles) of 2-ketobutyric acid, 1.13 g (10 mmoles) of 2,2-dimethylcyclopropanecarboxamide and 20 ml of toluene stirred at reflux for 10 hours. After cooling the crystalline solid was filtered and washed with toluene (3×10 ml) and dried to give 1.06 g of product, mp 140°–141° C. Tlc (4:1 toluene-AcOH) showed essentially one spot and the NMR spectrum fit the desired structure.

Recrystallization from EtOAc gave after drying 0.533 g of product mp 142°–143.5°, homogeneous by tlc.

| Anal. ($C_{10}H_{15}NO_3$) | Calcd. | Found |
| --- | --- | --- |
| C | 60.90 | 60.92 |
| H | 7.67 | 7.71 |
| N | 7.10 | 7.38 |

EXAMPLE 3

2-(2,2-Dimethylcyclopropanecarboxamido)-2-hexenoic acid

Step A: DL-Norleucine t-butyl ester

General procedure of R. Roeske, *J. Org. Chem.* 28, p. 1251 (1963).

To a suspension of 9.82 g (75 mmole) of DL-norleucine in 80 ml of dioxane in a 500 ml. pressure bottle cooled in an ice bath was added slowly (with swirling) 8 ml of concentrated $H_2SO_4$. The resulting mixture was cooled in a dry ice bath as 80 ml of liquid isobutylene was added. The mixture was allowed to warm to room temperature and shaken under autogenous pressure for ~23 hrs. After most of the isobutylene had been vented off, the slightly hazy solution was cooled in ice and then added to a cold mixture of 400 ml of 1N NaOH and 500 ml of $Et_2O$. After shaking in a separate funnel, the layers were separated, and the aqueous fraction was washed with an additional 100 ml of $Et_2$). The $Et_2O$ solution was shaken with 150 ml of 0.5 N HCl. The acidic aqueous fraction was treated with 2.5 N NaOH until strongly basic and then shaken with 250 ml of $Et_2O$. The $Et_2O$ solution was dried ($MgSO_4$), filtered, and concentrated on the rotovac. After prolonged pumping on high vacuum over a steam bath, final yield of clear, colorless residual oil=9.04 g (65%). NMR now showed only a trace of dioxane TLC (9:1 $CHCl_3$—MeOH) showed a single spot.

Step B: N-(2,2-Dimethylcyclopropanecarbonyl)-DL-norleucine t-butyl ester

To a solution of 8.98 g (48 mmole) of DL-norleucine t-butyl ester and 5.05 g (50 mmole) of triethylamine in 100 ml of $CH_2Cl_2$ stirred in an ice bath under a drying tube was added dropwise (over a period of 75 min.) a solution of 6.39 g (48 mmole) of 2,2-dimethylcyclopropanecarbonyl chloride (M. Elliot and N. R. James, British Patent No. 1,260,847 (1972)) in 50 ml of $CH_2Cl_2$. Precipitation of $Et_3N$ HCl occurred during the addition, especially toward the end. As the ice gradually melted, the mixture was allowed to warm to room temperature. After 16 hrs, the mixture was shaken with 200 ml of 0.5 N HCl. The $CH_2Cl_2$ fraction was washed with an additional 200 ml of 0.5 N HCl, then with 2×200 ml of 0.5 N NaOH, and finally 200 ml of $H_2O$. The $CH_2Cl_2$ fraction was dried with $MgSO_4$, treated with charcoal, and filtered through Celite. The filtrate was concentrated on the rotovac (finally under high vacuum). Yield of light orange residual oil=11.93 g (88%). Tlc (2:1 hexane-EtOAc) showed a single spot. NMR and IR were in accord with the assigned structure. After standing for several days, the unused portion of this material crystallized: m.p. 52°–>65°.

Step C: t-Butyl 2-(2,2-dimethylcyclopropanecarboxamido)-2-methoxyhexanoate

Based on procedure of H. Poisel and V. Schmidt, *Chem. Ber.*, 108 p. 2547 (1975).

To a solution of 6.37 g (22 5 mmole) of N-(2,2-dimethylcyclopropanecarbonyl)-DL-norleucine t-butyl ester in 35 ml of Et$_2$O stirred at room temperature under N$_2$ in the dark was added 2.69 ml (2.45 g, 22.5 mmole) of t-butyl hypochlorite. After 15 min., a solution of sodium methoxide prepared by dissolving 0.52 g (22.6 mmole) of sodium in 35 ml of MeOH was added. Stirring was continued at ambient temperature under N$_2$ in the dark. After 16.5 hrs., the precipitated NaCl was filtered off. The filtrate was diluted with Et$_2$O and washed successively with 3×50 ml of 0.5 N HCl, 50 ml of saturated Na CO$_3$, and 2×50 ml of H$_2$O. The E$_2$O phase was dried over MgSO$_4$ and filtered. The filtrate was concentrated on the rotovac. The pale, golden-yellow residual oil (6.45 g) was subjected to preparative high pressure liquid chromatography, resulting in the separation and isolation of 273 mg and 496 mg of the two diastereomers of t-butyl 2-(2,2-dimethylcyclopropanecarboxamido)-2-methoxyhexanoate (respective mp's 114°–118° and 124°–125.5°) as well as 1.97 g of a single isomer (apparently Z) of t-butyl 2-(2,2-dimethylcyclopropanecarboxamido)-2-hexenoate (colorless oil).

Step D:
2-(2,2-Dimethylcyclopropanecarboxamido)-2-hexenoic acid

A solution of 0.84 g (3.0 mmole) of t-butyl 2-(2,2-dimethylcyclopropanecarboxamido)-2-hexenoate in 10 ml of Et$_2$O saturated with anhydrous HCL was allowed to stand at room temperature under a drying tube. After 17 hrs, the solution was evaporated, and the residual gum was dissolved in 10 ml of saturated NaHCO$_3$. This solution was washed with an additional 15 ml of 0.5 N HCl, then dried (MgSO$_4$), filtered, and concentrated to give a viscous oil. The oil was crystallized from toluene. Yield of white crystals=0.32 g (47%), m.p. 119°–122°. TLC (4:1 toluene-AcOH) showed a single spot. NMR indicated essentially pure Z-isomer. (Note Treatment of the methanol adduct, t-butyl 2-(2,2-dimethylcyclopropanecarboxamido)-2-methoxyhexenoate, with anhydrous HCl in Et$_2$O under similar conditions gave the same product.)

EXAMPLE 4

(+)-Z-2-(2,2-Dimethylcyclopropanecarbonylamino)-2-octenoic acid, sodium salt

The reagents, (+)-2,2-dimethylcyclopropanecarboxamide, 7.0 g.; 2-keto-octanoic acid ethyl ester, 14.7 g.; 50 mg. of p-toluene sulfonic acid; and 100 ml. of toluene was changed to a 250 ml. three-necked flask under a Dean Stark trap containing several molecular sieve pellets. The mixture was refluxed vigorously for 27 hours. The resultant light yellow solution was cooled and concentrated in vacuo, at a water bath temperature of 45° C., in the presence of water to help remove toluene. The gummy residue was suspended in 230 ml. of 2N NaOH and stirred at 30° C. for 3 hours; then the temperature was raised to 35° C. for an additional 2½ hrs until a clear solution formed. The solution was then cooled, 85 ml. methylene chloride added, and the pH adjusted to 8.5 using 4N HCl with stirring. The organic layer was separated and discarded. The aqueous layer (366 ml.) was assayed by liquid chromatography to contain 37.2 mg/ml; 87% Z isomer. Another 85 ml. portion of CH$_2$Cl$_2$ was then added and pH adjusted to 4.5 with stirring. The organic layer was separated and the aqueous layer re-extracted with 50 ml. of CH$_2$Cl$_2$, with the pH again adjusted to 4.5. Combined organic extracts were dried over Na$_2$SO$_4$, filtered, and concentrated to a gum. This residue was dissolved in 150 ml. isopropanol and 15 ml. water and the pH adjusted to 8.2 with 2N NaOH. The resulting solution was concentrated to an oily residue which was flushed with isopropanol until it turned to a crystalline solid, indicating that most water had been removed. It was crystallized from 120 ml. of isopropanol, (cooled in ice for 1 hour) filtered, and washed with 50 ml. cold isopropanol followed by copious amounts of acetone. It was dried at 60° C./0.1 mm/2 hours to yield 10.74 g (63.2%) crystalline material, having essentially a single peak in liquid chromatography, m.p. 241°–243° C.

The starting material, (+)-2,2-dimethylcyclopropanecarboxamide is most conveniently prepared by resolution of the D,L acid, followed by reaction with oxalyl chloride and then ammonia to give the resolved amide.

One way of making the starting material is as follows: 23.1 g. of D,L-2,2-dimethylcyclopropanecarboxylic acid was suspended in 33 ml H$_2$O and the pH adjusted to 8.0, using 50% NaOH, about 10 ml. To this was added a solution of 38.4 g quinine in a mixture of 60 ml. methanol and 30 ml H$_2$O to which had been added about 8 ml of concentrated HCl in another 30 ml. H$_2$O to give a pH of 7.1. (This was actually a solution of quinine hydrochloride.)

These solutions were added all at once, with stirring. The gummy crystalline material which formed was heated to give two clear layers and again stirred vigorously while cooling to give a crystalline product. This product was permitted to stand over two days at room temperature. It was then filtered, washed with 2×10 ml water, and 2×10 ml 50% methanol, and air dried with suction. The yield of crude quinine salt was 44.8 g (48.7% yield) monohydrate, m.p. 113°–116° C., having a $[\alpha]_D^{20}$ of −94.3°, C=1.0; CHCl$_3$. This material was recrystallized from acetone to yield 24.35 g, m.p. 127°–130° C. This purified quinine salt was converted to the acid by reaction with aqueous base and chloroform, followed by acid, to yield (96%) 3.9 g having $[\alpha]_D^{20}$ of +146.0°.

This acid was converted to the amide as follows: A charge of 30.5 g (+)acid was added over 5–10 minutes through a dropping funnel to chilled (10° C.) oxalyl chloride, 54 ml., containing 1 drop dimethylformamide. This was stirred overnight at ambient temperature. A clear solution was observed, which was added to 100 ml. methylene chloride to dilute. Excess oxalyl chloride was removed by concentrating and the mixture flushed twice with methylene chloride.

The resultant solution was diluted with an equal volume of methylene chloride, and added continuously through a dropping funnel to about 100 ml anhydrous liquid ammonia which was diluted with 100 ml methylene chloride. A dry ice-acetone cooling bath was used during the addition. When all was added, the cooling bath was removed and the mixture stirred at room temperature for about ½ hour. The mixture was filtered, to remove precipitated ammonium chloride, and concentrated to dryness. The crude weight was 26.6 g. (88%) It was redissolved in excess hot ethyl acetate and filtered through a preheated sintered glass funnel to separate from trace NH$_4$Cl. Excess ethyl acetate was atmospherically distilled off. When half the volume remained, 130 ml of heptane were added, and ethyl acetate was continued to be distilled off, until the boiling point started to rise (to near 80° C.; much of product had already crystallized out). Heat was removed, and the mixture let cool gradually to about 30° C., then cooled with an ice bath to 0°–5° C. for about ½ hour. The product was recovered as nice silvery-white crystalline flakes, washed with 3×ethyl acetate/hexane mixture, 1/1 5 and air dried to constant weight. It weighed 23.3 g (77.1% yield overall, 87.6% recovery from crude), m.p. = 135°–138° C. (varies with rate of heating). Angle of rotation was determined by dissolving 0.0543 g in 10 ml chloroform, $[\alpha]_D^{20} = +100.9°$.

EXAMPLE 5

Z-2-(2,2-Dichlorocyclopropanecarboxamido)-2-butenoic acid

Step A: 2,2-Dichlorocyclopropanecarboxamide

A 7.1 g sample of 2,2-dichlorocyclopropanecarbonyl chloride (U.S Pat. No. 3,301,896, issued Jan. 31, 1967) was added dropwise to 75 ml of concentrated ammonium hydroxide with vigorous stirring. The temperature of the reaction mixture was maintained below 10° C. with an ice bath. The mixture was stirred in the ice bath for 30 min., then at room temperature for 1 hr. The aqueous ammonia was evaporated under reduced pressure (bath at 50° C.). The solid residue was extracted with hot ethyl acetate (3×30 ml). The extracts were boiled down to 40 ml and 20 ml of hexane was added. After cooling in ice, the solid was filtered, washed with ethyl acetate-hexane (1:1) and dried to give 2.7 g of 2,2-dichlorocyclopropanecarboxamide, m.p. 144°–146°. The NMR spectrum was in accord with the desired structure.

| Anal. ($C_{12}H_5Cl_2NO$) | Calcd. | Found |
| --- | --- | --- |
| C | 31.20 | 31.26 |
| H | 3.27 | 3.31 |
| N | 9.10 | 9.11 |
| Cl | 46.04 | 45.79 |

Another 1.3 g of amide, m.p. 143°–145° could be recovered from the mother liquor.

Step B:
Z-2-(2,2-Dichlorocyclopropanecarboxamido)-2-butenoic acid

A mixture of 1.53 g (15 mmoles) of 2-ketobutyric acid, 1.54 g (10 mmoles) of 2,2-dichlorocyclopropanecarboxamide and 10 ml of toluene was heated under reflux for 12 hrs. with removal of $H_2O$ by a modified Dean-Stark trap containing molecular sieves (4A). An additional 0.7 g of 2-ketobutyric acid was added and the reaction mixture was heated under reflux for an additional 12 hrs. The mixture was cooled, diluted with 20 ml of toluene and extracted with saturated sodium bicarbonate (3×10 ml). The extracts were combined, washed with ether and acidified to pH 3 (pH meter) with concentrated hydrochloric acid. A gum precipitated which soon solidified. It was filtered, washed with water, dried and recrystallized from nitromethane to give 423 mg of Z-2-(2,2-dichlorocyclopropanecarboxamido)-2-butenoic acid, m.p. 188°–189.5° C. The NMR spectrum was in accord with the desired structure.

| Anal. ($C_8H_9Cl_2NO_3$) | Calcd. | Found |
| --- | --- | --- |
| C | 40.36 | 40.48 |
| H | 3.81 | 3.80 |
| N | 5.88 | 5.91 |
| Cl | 29.78 | 29.53 |

EXAMPLE 6

Z-2-(2,2-Dichlorocyclopropanecarboxamido)-2-octenoic acid

A mixture of 1.19 g (7.5 mmoles) of 2-ketooctanoic acid, 0.77 g (5.0 mmoles) of 2,2-dichlorocyclopropanecarboxamide, and 5 ml toluene were reacted using the same procedure as in the previous example. The crude product (537 mg) was purified by conversion to the methyl ester ($BF_3/CH_3OH$), preparative TLC (silica gel G, 4:1 hexane-EtOAc) and saponification of the pure Z-methyl ester (0.3M $LiOH/CH_3OH$) to give 88 mg of Z-2-(2,2-dichlorocyclopropanecarboxamido)-2-octenoic acid as a partially crystalline gum. NMR spectrum (DMSO-$d_6$): 9.68 $\delta$(s, 1H, NH), 6.50$\delta$ (t, 1H, 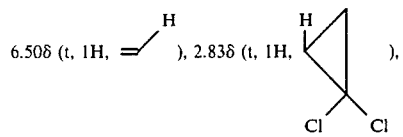 ), 2.83$\delta$ (t, 1H, 1.97$\delta$ (d, 2H 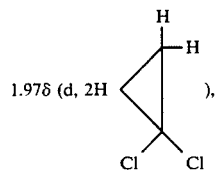 ), 0.87$\delta$(t, 3H, $CH_3$).

EXAMPLE 7

Z-8-Bromo-2-(2,2-Dimethylcyclopropanecarboxamido)-2-octenoic acid

To a suspension of 14.4 g (0.3 mole) of 50% NaH dispersion in 360 ml of toluene cooled in an ice bath and in a $N_2$ atmosphere was added over 45 min. a solution of 146 g (0.6 moles) of 1,6-dibromohexane and 57.6 g (0.3 mole) of ethyl 1,3-dithiane-2-carboxylate in 120 ml of DMF. The cooling bath was removed and the mixture stirred at room temperature for 2 hrs. The reaction mixture was washed with water (3×210 ml), dried over $MgSO_4$ and evaporated under reduced pressure to give 179.5 g of a yellow oil containing the desired anhydrated dithiane, 1,6-dibromohexane and mineral oil. This crude material was used in the next reaction without purification.

To a suspension of 426 g (2.4 moles) of N-bromosuccinamide in 800 ml of acetonitrile and 200 ml of $H_2O$ was added over 45 min. a solution of the crude dithiane in 100 ml of acetonitrile. The temperature of the reaction mixture was maintained below 25° C. with an ice bath. After stirring at 20° C. for 10 min. the dark red reaction mixture was poured into 2 l. of hexane-$CH_2Cl_2$(1:1). The solution was shaken with saturated $NaHSO_3$ (2×400 ml) and water (1×500 ml). Then 400 ml of saturated $Na_2CO_3$ solution was added in small portions (vigorous $CO_2$ solution). After the foaming subsided the funnel was shaken and the aqueous phase separated. The organic layer was extracted with saturated $Na_2CO_3$ solution (400 ml) and water (500 ml) and dried over $MgSO_4$. Removal of the solvent under reduced pressure gave 133.8 g of crude bromo ketoester containing 1,6-dibromohexane and mineral oil. This crude material was used in the next reaction without purification.

A mixture of 133.8 g of crude bromo ketoester, 133 ml of 50% hydrobromic acid and 267 ml of acetic acid was heated at 90° C. (internal temperature) for 75 min. The dark solution was evaporated under reduced pressure until most of the acetic acid was removed. The residue was dissolved in 500 ml of ether, washed with water (2×100 ml) and extracted with saturated $NaHCO_3$ (3×200 ml). The combined NaHCO extracts were extracted with ether (2×100 ml) and acidified with concentrated HCl. The precipitated oil was extracted with ether (3×200 ml). The ether extracts were washed with water (1×100 ml) and saturated brine (1×100 ml) and dried over $MgSO_4$. Removal of the ether under reduced pressure gave 46.2 g of pure bromoketo acid. Homogeneous by TlC (silica gel, 4:1 toluene-acetic acid). The NMR spectrum was consistent with the desired product.

A mixture of 46.1 g (0.194 moles) of the bromoketo acid, 17.6 g (0.156 mole) of 2,2-dimethylcyclopropanecarboxamide and 450 ml of toluene was heated under reflux for 13 hrs., with collection of water in a small Dean-Stark trap. After cooling, the clear reaction mixture was extracted with saturated $NaHCO_3$ solution (4×100 ml). The combined extracts were washed with ether (2×100 ml) and then the pH was adjusted to 3.5 (pH meter) by addition of concentrated HCl. An oil precipitated which soon crystallized. The solid was filtered, washed well with water and dried. Recrystallization from acetonitrile gave 22.5 g of Z-8-bromo-2-(2,2-dimethylcyclopropanecarboxamido)-2-octenoic acid, m.p. 151°-153° C. Homogeneous by TLC (4:1 tolueneacetic acid). The NMR spectrum was consistent with the desired structure.

| Anal. ($C_{14}H_{22}BrNO_3$) | Calcd | Found |
| --- | --- | --- |
| C | 50.61 | 50.66 |
| H | 6.67 | 6.96 |
| N | 4.22 | 4.45 |
| Br | 24.05 | 23.95 |

EXAMPLE 8

Z-8-Dimethylamino-2-(2,2-dimethylcycloproanecarboxamido)-2-octenoic acid

A solution of 664 mg (2 mmoles) of Z-8-bromo-2-(2,2-dimethylcyclopropanecarboxamido)-2-octenoic acid in 10 ml of 40% aqueous dimethylamino was allowed to stand at room temperature for 4 hrs. The solution was poured onto a 3.5×20 cm column of Dowex 50W-x8 (100-200 mesh, $H^+$) ion exchange resin and column eluted with water until the effluent was no longer acidic (~200 ml). The column was then eluted with 300 ml of 2N ammonium hydroxide. The effluent was evaporated under reduced pressure to give 600 mg of a colorless glass. This material was dissolved in 3 ml of ethanol, filtered, and added dropwise to 200 ml of rapidly stirred acetone. A gummy solid precipitated which crystallized upon stirring for two days. The solid was filtered, washed with acetone, and dried to give 445 mg of Z-8-dimethylamino-2-(2,2-dimethylcyclopropanecarboxamido)-2-octenoic acid as a colorless, hygroscopic crystals, m.p. 101°-112° C. Homogeneous by TLC (silica gel, in BuOH, HOAc, $H_2O$, 4:1:1). NMR spectrum was consistent with desired structure.

| Anal. ($C_{16}H_{28}N_2O_3 \cdot H_2O$) | Calcd. | Found |
| --- | --- | --- |
| C | 61.12 | 61.03 |
| H | 9.62 | 9.28 |

EXAMPLE 9

Z-2-(2,2-Dimethylcyclopropanecarboxamido)-8-trimethylammonium hydroxide-2-octenoic acid inner salt A solution of 996 mg (3 mmoles) of Z-8-bromo-2-(2,2-dimethylcyclopropanecarboxamido)-2-octenoic acid in 15 ml of 25% aqueous trimethylamine was allowed to stand at room temperature for 3 hrs. The reaction mixture was poured onto a 2×25 cm column of IRA-410 (50-100 mesh, $OH^-$) ion exchange resin and eluted with water until the effluent was no longer basic. The effluent was evaporated under reduced pressure to give 800 mg of a colorless glass. This material was dissolved in 20 ml of ethanol, filtered and diluted with 600 ml of acetone. After standing at room temperature overnight the crystalline solid which deposited was filtered, washed with acetone and dried to give 720 mg of Z-2-(2,2-dimethylcyclopropanecarboxamido)-8-trimethylammonium hydroxide-2-octenoic acid inner salt as hygroscopic crystals, m.p. 220°-222° C. Homogeneous by TLC (silica gel, in BuOH, HOAc, $H_2O$, 4:1:1). NMR spectrum was consistent with desired structure.

| Anal. ($C_{17}H_{30}N_2O_3$) | Calcd | Found |
| --- | --- | --- |
| C | 65.77 | 65.78 |
| H | 9.74 | 9.98 |
| N | 9.02 | 8.92 |

EXAMPLE 10

Z-2-(2,2-Dimethylcyclopropanecarboxamido)-8-formamidino-2-octenoic acid

A 350 mg sample of Z-8-amino-2-(2,2-dimethylcyclopropanecarboxamido)-2-octenoic acid was dissolved in 10 ml of water and the pH adjusted to 8.5 with 2.5N NaOH. A total of 947 mg of benzyl formimidate hydrochloride was added at room temperature in small portions over 20 min. while the pH was maintained between 8-9 by addition of 2.5N NaOH. After stirring at room temperature for 30 min., the cloudy reaction mixture was extracted with ether (3X) and applied to a 2×2.5 cm column of a G50W-X4 ($Na^+$, 200-400 mesh) resin. After elution with water, the fractions containing the product were pooled and evaporated under reduced pressure. This material was dissolved in water and applied to a 2×25 cm column of a GlX8 ($HCO_3^-$, 200-400 mesh) resin. After elution with water, the fractions containing pure product were pooled and evaporated under reduced pressure. The residue was dissolved in a few ml of warm ethanol, filtered, and added dropwise to 200 ml of ether with rapid stirring. Filtration and washing with ether gave 243 mg of Z-2-(2,2-dimethylcyclopropanecarboxamido)-8-formamidino-2-octenoic acid as an amporphous solid. Homongeneous by TLC n-BuOH, HOAc, $H_2O$; 4:1:1). The NMR spectrum was in accord with the desired structure.

| Anal. ($C_{15}H_{25}N_3O_3 \cdot \frac{1}{2}H_2O$) | Calcd. | Found |
|---|---|---|
| C | 59.69 | 60.04 |
| H | 8.59 | 8.64 |
| N | 13.92 | 13.57 |

EXAMPLE 11

Z-2-(2,2-Dimethylcyclopropanecarboxamido)-8-guanidino-2-octenoic acid

To a solution of 2 mmoles of guanidine (prepared from 432 mg of guanidine sulfate and 630 mg of barium hydroxide octahydrate) in 7 ml of water was added 332 mg (1 mmole) of 8-bromo-2-(2,2-dimethylcyclopropanecarboxamido)octenoic acid, and the solution was heated at 70° C. in a nitrogen atmosphere for 1 hr. The reaction mixture was applied to a 2×25 cm column of Dowex 50W-X8 (H +, 100–200 mesh). After elution with water the fractions containing the product were pooled and evaporated under reduced pressure. The residue was dissolved in several ml of warm ethanol and added dropwise to 100 ml of ether with rapid stirring. Filtration and washing with ether gave 107 mg of Z-2-(2,2-dimethylcyclopropanecarboxamido)-8-guanidino-2-octenoic acid as an amorphous electrostatic powder. Homogeneous by TLC (n-BuOH, HOAc, $H_2O$; 4:1:1). NMR ($D_2O$, NaOD):

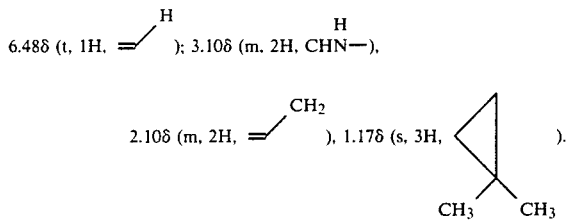

EXAMPLE 12

Z-2-(2,2-Dimethylcyclopropanecarboxamido)-8-methyl-2-octenoic acid

To a solution of 2.43 mmoles of sodium methoxide in 5 ml of methanol was added 332 mg (1 mmole) of 8-bromo-2-(2,2-dimethylcyclopropanecarboxamido)-2-octenoic acid. The solution was heated under reflux in a nitrogen atmosphere for 1 hr. The reaction mixture was evaporated under reduced pressure, the residue dissolved in water and acidified with 2.5 N hydrochloric acid. The oil which precipitated was extracted with ether (3X). The ether extracts were washed with water, and saturated brine and dried over $MgSO_4$. Removal of the ether under reduced pressure gave a colorless oil that crystallized upon standing. It was recrystallized from ether-hexane to give 140 mg of Z-2-(2,2-dimethylcyclopropanecarboxamido)-8-methoxy-2-octenoic acid, m.p. 71°–72° C. Homogeneous by TLC (toluene-HOAc, 4:1). The NMR spectrum was in accord with the desired structure.

| Anal. ($C_{15}H_{25}NO_4$) | Calcd. | Found |
|---|---|---|
| C | 63.58 | 63.54 |
| H | 8.89 | 9.12 |
| N | 4.94 | 5.16 |

EXAMPLE 13

Z-8-[(Carboxymethyl)methylamino]-2-(2,2-dimethylcyclopropanecarboxamido)-2-octenoic acid 3.32 g of Z-8-bromo-2-(2,2-dimethylcyclopropanecarboxamido)-2-octenoic acid, 1.0 g of $CH_3NHCH_2CO_2H$, 3.5 g of $Na_2CO_3$ and 30 ml of water were heated at 80° C. in $N_2$ for 1.5 hours. After purification, 1.01 g of product was prepared, calc for $C_{17}H_{28}N_2O_5 \cdot 2H_2O$: C, 54.24; H, 8.57; N, 7.44; found: C, 54.40; H, 8.34; N, 7.16.

EXAMPLE 14

Z-2-(2,2-dimethylcyclopropanecarboxamido)-8-[1-(phosphono)ethylamino]-2-octenoic acid was prepared reacting the same bromo intermediate (335.1 gm) with 138.2 mg 1-aminoethane phosphoric acid, 435 mg $Na_2CO_3$ in 5 ml water, following essentially the same procedure.

EXAMPLE 15

7-(L-amino-2-carboxyethylthio)-2-(2,2-dimethylcyclopropanecarboxamido)-2-heptenoic acid It is prepared in a similar fashion as the above example, except that Z-7-bromo-2-(2,2-dimethylcyclopropanecarboxamido)-2-heptenoic acid (185 mg, 105 mmoles) is dissolved in 2.02 ml NaOH solution (2.0 N), and deoxygenated by bubbling a stream of nitrogen gas through it for one minute. Then cysteine HCl (185 mg, 1.05 mmoles) is added all at once and the reaction stirred at room temperature in a $N_2$ atmosphere for 3 hours. The reaction mixture is applied to 2×20 cm column of Dowx 50×4 (100–200 mesh, H+), and eluted with 300 ml $H_2O$, then 200 ml of 2N $NH_3$ solution Ammonia evaporated under reduced pressure to give 284 mg of a yellowish glass. This product is dissolved in 4 ml ethanol, and the insoluble material filtered. The filtrate is added dropwise to rapidly stirred diethylether (150 ml). The solid which precipitates is filtered, washed with ether and dried to yield 171 mg product, having one spot (ninhydrin positive) in TLC (nBuOH, HOAc, $H_2O$; 4:1:1) rf. about 6; NMR is consistent with desired structure. Anal. ($C_{16}H_{26}N_2O_5S$) Calcd. C, 53.61; H, 7.31; N, 7.81; S, 8.94. Found: C, 52.55; H, 7.40; N, 7.89; S, 9.63.

EXAMPLE 16

Sodium Z-7-(L-amino-2-Carboxyethylthio)-2-(2,2-dimethylcyclopropanecarboxamido)-2-heptenoic acid A. Grignard Preparation of Ethyl-7-chloro-2-oxo-heptenoate Equimolar amounts (8 moles each) of 1-bromo-5-chloropentane and magnesium are reacted in tetrahydrofuran (960 ml) at 25° C. The flask is changed with Mg in the THF and the bromochloropentane added over 1 hour, then aged 2 hours. After the reaction was judged complete the reaction solution was added (cooled to −15° C.) to 16 moles of diethyloxalate in 1856 ml tetrahydrofuran, while maintaining the temperature at −10° C. 3N HCl was added to quench, keeping the temperature below 25° C. After strippiing solvents, a calculated yield of 48.8% of the ethyl-1-chloro-6-oxoheptenoate was recovered.

B. Condensation and Hydrolysis

S-2,2-dimethylcyclopropylcarboxamide (1017 g), 2143.6 g of ethyl-7-chloro-2-ketoheptanoate, 9 liters of toluene and 12 g of p-toluene sulfonic acid were charged to a 22 L. flask, and heated to reflux with stirring. After 23 hours, liquid chromatography showed the expected product ratio, and 4 L. of toluene were removed under slightly reduced pressure. The pot was charged with water, neutralized to pH 7 with 2N NaOH, and vacuum distilled leaving a final pot volume of about 5 liters.

This was hydrolyzed by adding 1760 g of 50% ag. NaOH (4 liters water) and stirring overnight.

The flask was charged with 4 L. methylene chloride, and pH adjusted to 8.8 using HCl bureacted amide crystallized out. The organic layers were separated from water, and then evaporated. The gummy residue was dissolved in 8 L. water containing 720 g 50% NaOH, and to this solution was charged 1818 g L. cysteine HCl.$H_2O$, 2 kg ice, 2484 g 50% NaOH and 1 L. water.

The pH of this solution, after aging overnight at room temperature, is adjusted to 3.0 with conc Hcl, and the resulting gummy suspension heated to 95° C. to afford a clear solution. After 30 minutes, no E isomer could be detected by lc. After work-up and purification, the overall yield was 50%. This material was recrystallized from acetonitrile. 1500 g of the recrystallized material was dissolved in 6 L water and 910 ml 3.88 N NaOH, then neutralized to pH 7, and lyophilized to afford 1569 g (98.6%) of the title compound; Analysis. Calcd; C, 50.52; H, 6.62; N, 7.36; S, 8.43; Na, 6.04. Found: C, 50.71; H, 6.78; N, 7.49; S, 8.52; Na, 5.92.

EXAMPLE 17

Z-8-[(2-Amino-2-oxoethyl)thio]-2-(2,2-dimethylcyclopropanecarboxamido)-2-ocetenoic acid This was also prepared in a similar manner to that described in Example 16, above, using 3.3 gm of the bromo intermediate, 1.3 g of $H_2NC(=O)CH_23H$, in 50 ml methanol. 1.6 gms of product, mp. 127°–128° C. was obtained.

EXAMPLE 18

The Z-8-cyano-2-(2,2-dimethylcyclopropanecarboxamido)-2-octenoic compound was prepared from 332 mg 8-bromo-2-(2,2-dimethylcyclopropanecarboxamido)-2-octenoic acid and 100 mg NaCN in 2 ml DMSO, heated at 80° C. for 30 min. After extraction and purification, 102 mg of a colorless solid, mp 99°–103° C. were recovered, analysis for $C_{15}H_{22}N_2O_3$: calcd, C, 64.73; H, 7.97; N, 10.06; found: C, 64.69; H, 8.14; N, 9.41.

EXAMPLE 19

Racemic
Z-7(3-hydroxy-2-pyridylthio)-2-(2,2-dimethylcyclopropanecarboxamide)-2-heptenoic acid A solution of 200 mg (0.630 mmole) of Z-7-bromo-2-(2,2-dimethylcyclopropanecarboxamide)-2-heptenoic acid, 72.4 mg (0.57 mmole) of 2-mercapto-3-pyridinol, and 134 mg (1.26 mmole) of $Na_2CO_3$ in 1.0 ml of $H_2O$ was stirred at room temp. under nitrogen.

Tlc (8:1 toluene:ACOH) showed a trace of 2-mercapto-3-pyridinol and remaining bromo compound.

The reaction mixture was partitioned between 10.0 ml of 1.5 N HCl and 10.0 ml $Et_2O$. The aqueous fraction was adjusted to pH~3.5 with 2.5 N NaOH. The product did not oil out, but was extracted into $Et_2O$, dried with $MgSO_4$ and filtered. Conc. of $Et_2O$ gave 151.0 mg of white crystalline product. This product was recrystallized from nitroethane with several drops of acetic acid, yield 43.0 mg, m.p. 199.0°–200.5° C.; and analysis gave for $C_{18}H_{23}N_2O_4S.5\ H_2O$, MW=373.46:

|   | Calcd. | found |
|---|--------|-------|
| N | 7.50   | 7.21  |
| C | 57.89  | 58.17 |
| H | 6.75   | 6.72  |
| S | 8.59   | 8.70  |

EXAMPLE 20

(+)-Z-2-(2,2-Dimethylcyclopropanecarboxamido)-7-(3-hydroxy-2-pyridylthio)-2-heptenoic acid A mixture of 2.00 g (6.3 mmole) of (+)-Z-7-bromo-2-(2,2-dimethylcyclopropanecarboxamido)-2-heptenoic acid 0.73 g (5.75 mmole) of 2-mercapto-3-pyridinol, 1.34 g (12.6 mmole) of $Na_2CO_3$, and 8 ml of $H_2O$ was stirred at room temperature under $N_2$. After 17.5 hrs the mixture was treated cautiously with 60 ml of 2.5 N HCl (foaming) and shaken with 60 ml of $Et_2O$ in a sep. funnel until all of the gummy precipitate obtained initially upon acidification had dissolved in one phase or the other. The aqueous phase was adjusted to pH 3.35 with 2.5 N NaOH, causing separation of a gum. The mixture was heated on a steam bath, resulting in a solidification. After cooling, the solid was collected on a filter and washed with $H_2O$.

The air-dried material (1.7 g) was suspended in ~50 ml of nitromethane, heated on a steam bath, and treated slowly with AcOH while hot until all of the solid dissolved. The solution was treated with charcoal and filtered through Super-Cel. The filtrate was reheated to redissolve crystallized product and then allowed to cool slowly. After standing, the crystallized product was collected on a filter and washed with nitromethane. The material was finally dried in a vacuum oven at 100°. Yield of white crystals = 1.24 g (59%), mp 188.5°–189°. Tlc (2:1 toluene-AcOH) was virtually homogenous. NMR (DMSO-$d_6$) was consistent with the assigned structure. From the mother liquor was obtained a second crop of light cream-colored crystals: 0.12 g, mp 185°–186°; tlc similar to that of first crop. Total yield of material=1.36 g (65%).

$[\alpha]_D^{27} = +34.3°$.

Anal. ($C_{18}H_{24}N_2O_4S$) Calcd: C 59.32; H, 6.64; N, 7.69; S, 8.80; Found (1st crop) C, 59.28; H, 6.58; N, 7.58; S, 8.96.

EXAMPLE 21

Racemic
Z-7-(3-carboxy-2-pyridylthio-2-(2,2-dimethylyclopropanecarboxamido)-2-heptenoic acid A solution of 108.0 mg (0.34 mmole) of Z-7-bromo-2-(2,2-dimethylcyclopropanecarboxamide)-2-heptenoic acid 48.0 mg (0.31 mmole) of 2-mercaptonicotinic acid, and 72.1 mg (0.68 mmole) of $Na_2CO_3$ in 0.5 ml $H_2O$ was stirred under $N_2$ at room temp.

After 1 day, the reaction mixture was partitioned between 2.5 N HCl and $Et_2O$. The product was extracted into 2.5 N HCl and to this layer was added 50%

NaOH until pH~2.5-3.0. The product was extracted into Et$_2$O dried with MgSO$_4$, filtered and concentrated on the rotovac to yield 51.0 mg (38%), with purity confirmed by NMR and tlc.

EXAMPLE 22

N-Formimidoyl thienamycin, crystalline

Step A. Benzylformimidate hydrochloride

A 3 l. three-necked flask fitted with an addition funnel, overhead stirrer, and a reflux condenser, was charged with a mixture of benzyl alcohol (125 g., 1.15 mol) formamide (51 g., 1.12 mol) and anhydrous ether (1200 ml.). The mixture was stirred vigorously at room temperature (20°-25° C.) under a nitrogen atmosphere and benzoyl chloride (157 g., 1.12 mol) in 50 ml. of anhydrous ether was added dropwise using the addition funnel. The addition required approximately 50 minutes.

The reaction mixture was stirred an additional 60 minutes at room temperature. The ether was removed by decantation and 300 ml. of acetic anhydride in 500 ml. of anhydrous ether was added. The mixture was stirred 30 minutes at room temperature. The precipitate was allowed to settle and the etheracetic anhydride was again removed by decantation. The solid was collected by filtration, washed with 500 ml. of ether and dried in vacuo over KOH at 25° C. for 2 hrs. to give 130 g. (67%) of benzylformimidate hydrochloride as a white solid.

The product was assayed by NMRδ(DMSO) 5.7 (s, 2H, φCH$_2$), 7.5 (s, 5H, φ), 9.0 (s, 1H, HC=N). The product is thermally unstable. It decomposes to formamide and benzyl chloride at 0° C. and above. However, no appreciable decomposition was detected on storage at −20° C. for 2 months.

Step B. Derivatization of Thienamycin

Thienamycin (in the form of a 6 l. aqueous solution, pH=6.5, concentrate from the fermentation broth, containing 28 g. thienamycin) was placed in a large beaker (12 l) and cooled to 0° C. The beaker was equipped with a pH meter and an efficient high speed stirrer. The pH was raised to 8.5 by the careful addition of 3N KOH (KOH was added dropwise via syringe to the stirred solution). The solution was treated with 6 equivalents of solid benzyl formimidate hydrochloride (~100 g.) in portions while maintaining the pH at 8.5±0.3 by the addition of 3N KOH (200 ml.) using a syringe. The addition required 3-5 min. The reaction mixture was stirred for 6 min. at 0° C. and then assayed by liquid chromatography to insure completion of the reaction. The solution was adjusted to pH 7 with 1N HCl. The volume of the reaction mixture was measured, and the solution was assayed by UV. The neutralized reaction mixture was concentrated to 15 g./l. on the reverse osmosis unit at <10° C. The volume of the concentrate was measured and the pH was adjusted to 7.2-7.4, if necessary. The concentrate was filtered through a medium porosity sintered glass funnel to remove any solids present after concentration.

Step C. Dowex 50W×2 Chromatography

The concentrate (750-1000 ml., 15-20 g.) was applied to 0° C. to a precooled 18 l. column of Dowex 50W×2 in the potassium cycle (200-400 mesh resin) and the column was eluted at 0°-5° C. with distilled deionized water a flow rate of 90 ml/min. and a head pressure of 0-45 psig.

Forerun fractions of 4 l., 2 l., and one l., were collected followed by 18 fractions of 450 ml. each, and one final fraction of 2 l. Each fraction was assayed by UV (1/100 dilution, NH$_2$OH extinction was omitted) and the total amount of NFT present in each fraction was calculated. The beginning and end fractions were assayed for liquid chromatography purity and the desired rich cut fractions were combined. The pH of the combined rich cuts was determined by both pH meter and bromothymol blue indicating solutions and was adjusted to pH 7.2-7.4 if necessary. The combined rich cuts (3-4 l.) were then assayed by UV and the total formamidine content was determined, 15-16 g., 75% yield from the column. The rich cuts were concentrated on the reverse osmosis unit at <10° C. as far as possible, then the concentration to 33 g./l. was completed on the circulatory evaporator at less than 28° C. A total volume of about 500 ml. concentrate was obtained.

Step D. Crystallization of N-Formimidoyl Thienamycin

The concentrate from the previous step is adjusted to 7.3, if necessary, and N-formimidoyl thienamycin content assayed by UV, was about 85-90%. The concentrate was filtered through a sintered glass funnel (medium porosity) into a large Erlenmeyer flask. Five volumes (~2200 ml.) of 3 A ethanol was filtered into the concentrate and the solution was stirred at room temperature for 10 minutes and at 0° C. for 12-24 hrs.

The crystals were filtered by suction filtration and washed with 0.1 volume (~250 ml.) of 0° C. 80% 3A ethanol followed by 1/25 volume (100 ml.) of 3 A ethanol at room temperature. The crystals were dried in vacuo for 12-24 hrs. to give approximately a 40% overall yield of N-formimidoyl thienamycin (10-12 g.).

Analytical results on a 50 g. blend of N-formimidoyl thienamycin, prepared as above, are as follows:

C, theory 45.42%; found, 45.82%
H, theory 6.03%; found, 5.72%
N, theory 13.24%; found, 13.10%
S, theory 10.10%; found, 10.14%
residue on ignition, predicted 0.5, found 0.47%;
$[\alpha]_D^{25} = 89.4°$, T.G.=6.8%, UVλmax 300 MM, E%=328.

EXAMPLE 23

Activity of DMCO with NFT

The compound N-formimidoyl thienamycin (NFT) and the compound Z-2-(2,2-dimethylcylcopropane carboxamido-2-octenoic acid (DMCO) were tested in rabbits to evaluate nephrotoxicity.

Either NFT alone or in combination with DMCO was administered intravenously to rabbits. After 48 hours blood samples were taken for determination of BUN and creatinine concentrations and the rabbits were killed for histologic examination of kidney sections.

The study was initiated with 28 New Zealand white rabbits which ranged in age from 23 to 27 weeks, and in weight from 2.78 to 3.71 kg for males and 2.81 to 3.85 kg for females. All animals were housed in individual stainless steel cages and maintained in climate-controlled rooms with access to food (Purina Rabbit Chow) and tap water ad libitum.

NFT was administered to six groups of 2 male and 2 female rabbits each at a nominal dose of 180 mg/kg. Five of these groups received DMCO in addition to NFT at nominal doses of 90, 30, 10, 3 or 1 mg/kg. All doses were administered via the marginal ear vein at a dosage volume of 1.89 ml/kg. An additional group of 2 male and 2 female rabbits received 0.9% sterile saline and served as controls.

NFT was dissolved in solutions of sodium bicarbonate (NFT alone group) or sterile solutions of DMCO in sodium bicarbonate at five different concentrations; these solutions were prepared immediately prior to use.

The mean BUN and serum cretinine concentrations and the degrees of renal tubular epithelial necrosis are shown below in Table I:

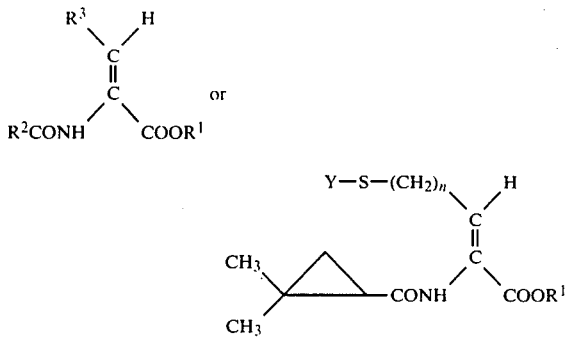

TABLE I

| Group No. | NFT (mg/kg) | DMCO (mg/kg) | BUN (mg/100 ml) | Creatinine (mg/100 ml) | Renal Tubular Necrosis* |
|---|---|---|---|---|---|
| I (Control) | 0 | 0 | 20.2 | 1.1 | None (0/4) |
| II | 180 | 0 | 70.0$^S$ | 4.2$^S$ | Marked-Severe (4/4) |
| III | 180 | 90 | 16.6$^{NS}$ | 1.2$^{NS}$ | None (0/4) |
| IV | 180 | 30 | 26.1$^{NS}$ | 1.3$^{NS}$ | V.Sl.-Moderate (4/4) |
| V | 180 | 10 | 53.1$^S$ | 2.9$^S$ | Moderate-Marked (4/4) |
| VI | 180 | 3 | 65.8$^S$ | 4.2$^S$ | Marked (4/4) |
| VII | 180 | 1 | 64.7$^S$ | 4.2$^S$ | Marked-Severe (4/4) |

*Numbers in parenthesis show numbers of rabbits with renal tubular necrosis/numbers of rabbits tested.
$^S$Statistically significantly (P ≦ 0.05) different from control.
$^{NS}$Not statistically significantly (P > 0.05) from control.

EXAMPLE 24

Activity of DMCO with Cephaloridine

A 48 hour intravenous study was performed in rabbits to investigate the effect of DMCO on the nephrotoxicity of cephaloridine.

Five groups of 2 male and 2 female rabbits received a single dose of one of the following: saline, DMCO (90 mg/kg), cephaloridine (180 mg/kg), cephaloridine (180 mg/kg)+DMCO (90 mg/kg).

All rabbits were sacrificed approximately 48 hours post-injection and both kidneys were removed, weighed, and samples of both kidneys were processed for microscopic examination.

The incidence and degree of renal proximal tubular necrosis are given below in Table II:

| Treatment Group | Renal Tubular Necrosis (incidence) | | | | |
|---|---|---|---|---|---|
| | None | V. Slight | Slight | Moderate | Marked |
| Saline | 4 | 0 | 0 | 0 | 0 |
| DMCO (90 mg) | 4 | 0 | 0 | 0 | 0 |
| Cephaloridine (180 mg) | 0 | 0 | 0 | 1 | 3 |
| Cephaloridine + DMCO (180 + 90 mg) | 2 | 1 | 1 | 0 | 0 |

What is claimed is:

1. A method of preventing the nephrotixic effect in animals of an antibiotic which is cephaloridine, which comprises co-administering to the animal A. from about 0.1 to 3 parts by weight of a 3-substituted propenoate of either of the following formula:

wherein (1) $R^2$ and $R^3$ are hydrocarbon radicals in the range respectively of 3-10 and 1-15 carbon atoms; in either one of these $R^2$ or $R^3$ hydrocarbon chains 1-6 hydrogens may be replaced by halogens or a non-terminal methylene may be replaced by oxygen or sulfur, including oxidized forms of the latter; (2) a terminal hydrogen in $R^3$ can also be replaced by (a) a hydroxyl or thiol group, which may be acylated or carbamoylated; (b) by an amino group, which may be derivatized as an acylamino, ureido, amidino, guaniino, alkyl or substituted alkyl amino group, or quaternary nitrogen group (c) by acid groups selected from the group consisting of carboxylic, phosphonic and sulfonic acid groups and combinations thereof, and salts, esters and amides thereof, (d) by cyano; (e) by terminal amino acid groups, or combinations thereof, and $R^1$ is hydrogen or lower alkyl ($C_{1-6}$) or dialkylaminoalkyl, or a pharmaceutically acceptable cation; and n is an integer from 3 to 5 and Y is pyridyl, pyrimidinyl, tetrazolyl, imidazolyl, thiadiazolyl or phenyl optionally substituted by hydroxy, oxo, carboxyl, or methyl; or a terminal amino acid group; and B. to 1 part by weight of said antibiotic.

2. The method of claim 1 in which $R^2$ is 2,2-dimethylcyclopropyl.

3. The method of claim 1 in which $R^2$ is 2,2-dichlorocyclopropyl.

4. The method of claim 3 in which the 3-substituted propenoic acid is Z-2-(2,2-dimethylcyclopropane carboxamido)-8-trimethyl ammonium-2-octenoic acid.

5. The method of claim 3 in which the 3-substituted propenoic acid is Z-2-(2,2-dimethylcyclopropane carboxamido)-2-butenoic acid.

6. The method of claim 3 in which the 3-substituted propenoic acid is Z-2-(2,2-dimethylcyclopropane carboxamido)-2-pentenoic acid.

7. The method of claim 3 in which the 3-substituted propenoic acid is Z-2-(2,2-dimethylcyclopropanecarboxamido)-2-octenoic acid.

8. The method of claim 3 in which the propenoate is Z-2-(2,2-dimethylcyclopropane carboxido)-2-hexenoic acid.

9. The method of claim 3 in which the 3-substituted propenoic acid is Z-8-[(carboxymethyl)methylamino]-2-(2,2-dimethylclyclopropanecarboxamido)-2-octenoic acid.

10. The method of claim 3 in which the 3-substituted propenoic acid is Z-8-[(2-amino-2-oxoethyl)thio]-2-(2,2-dimethylcyclopropanecarboxamido)-2-octenoic acid.

11. The method of claim 3 in which the 3-substituted propenoic acid is Z-2-(2,2-dimethylcyclopropanecarboxamido)-8-[1-(phosphono)ethylamino]-2-octenoic acid.

12. The method of claim 3 in which the 3-substituted propenoic acid is Z-7-(L-amino-2-carboxyethylithio)-2-(2,2dimethylcyclopropanecarboxamido)-2-heptenoic acid.

13. The method of claim 3 in which the 3-substituted propenoic acid is Z-8-acetamido-2-(2,2-dimethylcyclopropanecarboxamido)-2-octenoic acid.

14. The method of claim 1 in which the propenoate is Z-7-(3-hydroxyl-2-pyridylthio)-2-(2,2-dimethylcyclopropanecarboxamido)-2-heptenoic acid.

15. The method of claim 1 which the propenoate is Z-(3-carboxyl-2-pyridylthio)-2-(2,2-dimethylcyclopropanecarboxamido)-2-heptenoic acid.

16. An antibacterial composition comprising a combination of cephaloridine and a 3-substituted propenoate as defined in claim 1, the ratio of cephaloridine to the propenoate being within the range of about 1 to 0.1-3.

17. The composition of claim 14 in which the combination is mixed with a pharmaceutical carrier.

18. The composition of claim 15 in which the carrier is adapted for injection.

19. The method of preventing the nephrotoxic effect in animals of an antibiotic which is thienamycin, N-guanyl, or N-forminmidoyl thienamycin, which comprises co-administering to the animal from about 0.1 to 3 parts by weight of (1) a 3-substituted propenoic acid selected from Z-2-isovaleramido-2-pentenoic acid; methyl Z-2-isovaleramido-2-butenoate; Z-2-isovaleramido-2-butenoic acid; Z-2-benzamido-2-butenoic acid; Z-2-(3,5,5-trimethylhexanamido)-2-butenoic acid; Z-2-cyclobutanecarboxamido-2-butenoic acid; Z-2-cyclopropanecarboxamido-2-butenoic acid; Z-2-cyclopropanecarboxamido- 2-pentenoic acid; Z-2-(3-methylvaleramido)-2-butenoic acid; Z-2-cycloheptanecarboxamido-2-butenoic acid; Z-2-nonamamido-2-butenoic acid; Z-2-cyclohexanecarboxamido-2-butenoic acid; Z-2-(4-methylvaleramido)-2-butenoic acid; Z-2-t-butylacetamido-2-butenoic acid; Z-2-octanamido-2-butenoic acid; Z-2-butyramido-2-butenoic acid; Z-2-valeramido-2-butenoic acid; Z-2-valeramido-2-pentenoic acid; Z-2-cyclopentanecarboxamido-2-butenoic acid; Z-2-(6-methylheptanamido)-2-butenoic acid; Z-2-hexanamido-2-butenoic acid; Z-2-(3,7-dimethyloctanamido)-2-butenoic acid; Z-2-(3,7-dimethyl-6-octenamido)-2-butenoic acid; Z-2-(5-chlorovaleramido)-2-butenoic acid; Z-2-(3-chlorobenzoylamido)-2-butenoic acid; Z-2-(2-chlorobenzamido)-2-butenoic acid; Z-2-(6-bromohexanamido)-2-butenoic acid; Z-2-(3,3-dimethylpropenamido)-2-butenoic acid; Z-2-benzamido-2-cinnamic acid; Z-2-benzamido-2-pentenoic acid; Z-2-benzamido-5-methoxy-2-pentenoic acid; Z-2-benzamido-2-hexendioic acid; Z-2-isovaleramido-2-octenoic acid; Z-2-isovaleramido-2-cinnamic acid; Z-2-isovaleramido-2-hexenedioic acid; Z-2-cyclopropanecarboxamido-2-cinnamic acid; Z-2 -cyclopropanecarboxamido-2-hexenendioic acid; Z-2-(5-methoxy-3-methylvaleramido)-2-butenoic acid; Z-2-ethylthioacetamido-2-butenoic acid; Z-2-(2,2-dichlorocyclopropanecarboxamido)-2-butenoic acid; Z-2-(2-ethylhexanamido)-2-butenoic acid; Z-2-di-n-propylacetamido-2-butenoic acid;

Z-2-(2,2-dimethylcyclopropanecarboxamido)-2-butenoic acid; (+)-Z-2-(2,2-dimethylcyclopropanecarboxamido)-2-butenoic acid; Z-2-(2,2-dimethylcyclclopropanecarboxamido)-2-pentenoic acid; Z-2-(2,2-dimethylcyclopropanecarboxamido)-2-octenoic acid; Z-2-(2,2-dimethylcyclopropanecarboxamido)-2-hexenoic acid; Z-2-(2,2-dimethylcyclopropanecarboxamido)- 2-cinnamic acid; Z-2-(2,2-dimethylcyclopropanecarboxamido)-5-methoxy-2-pentenoic acid; Z-2-(2,2-dimethylcyclopropanecarboxamido)-4,4,4-trifluoro-2-butenoic acid; Z-2-(2,2-dimethylcyclopropanecarboxamido)-3-(2-chlorophenyl)-propenoic acid; Z-2-(2,2-dimethylcyclopropanecarboxamido)-2-hexenedioic acid; Z-2-(2-ethylcyclopropanecarboxamido)-2-butenoic acid; Z-2-(2,2-diethylcyclopropanecarboxamido)-2-butenoic acid; Z-2-(2,2-diethylcyclopropanecarboxamido)-2-pentenoic acid; Z-2-(2-isopropyl-2-methylcyclopropanecarboxamido)-2-butenoic acid; Z-5-cyano-2-(2,2-dimethylcyclopropanecarboxamido)-2-pentenoic acid; Z-5-(N,N-dimethylcarbamoyl)-2-(2,2-dimethylcyclopropanecarboxamido)-2-pentenoic acid; Z-2-(2,2-dimethylcylpropanecarboxamido)-5-methanesulfonyl-2-pentenoic acid; Z-2-(2,2-dimethylcyclopropanecarboxamido)-5-ethyoxycarbonyl-2-pentenoic acid; Z-2-(2-methylcyclopropanecarboxamido)-2-butenoic acid; methyl Z-2-(2,2-dimethylcyclopropanecarboxamido)-2-butenoate; ethyl Z-2-(2,2-dimethylcyclopropanecarboxamido)-2-bitempate; 2-dimethylaminoethyl ester of Z-2-(2,2-dimethylcyclopropanecarboxamido)-2-butenoic acid; 3-diethylaminopropyl ester of Z-2-(2,2-dimethylcyclopropanecarboxamido)-2-pentenoic acid; Z-2-(2,3-dimethylcyclopropanecarboxamido)-2-butenoic acid; Z-2-(3,3-dimethylcyclobutanecarboxamido)-2-butenoic acid; Z-2-(2-spirocyclopentanecarboxamido)-2-butenoic acid; Z-2-(2-t-butyl-3,3-dimethylcyclopropanecarboxamido)-2-butenoic acid; Z-2-(2,2-dimethylcyclopropanecarboxamido)- 4-methyl-2-pentenoic acid; Z-2-(2-t-butylcyclopropanecarboxamido)-2-butenoic acid; Z-2-(2-phenylcyclopropanecarboxamido)-2-butenoic acid; Z-3-cyclohexyl-2-(32-dimethylcyclopropanecarboxamido)propenoic acid; Z-5-carboxy-5-(2,2-dimethylcyclopropanecarboxamido)-4-pentenamidine; Z-5-dimethyl amino-2-(2,2-dimethylcyclopropanecarboxamido)-2-pentenoic acid; Z-3-cyclopropyl-2-(2,2-dimethylcyclopropanecarboxamido)propenoic acid; Z-2-(2,2-dimethylcyclopropanecarboxamido)-2,5-hexadienoic acid; Z-2-(2,2-dimethylcyclopropanecarboxamido)-4-phenyl-2-butenoic acid; Z-2-(2,2-dimethylcyclopropanecarboxamido)-6-mercapto-2-hexenoic acid; Z-2-(2,2-dimethylcyclopropanecarboxamido)-5-methylthio-2-pentenoic acid; Z-2-(2,2-dimethylcyclopropanecarboxamido)-5-phosphono-2-pentenoic acid; Z-2-(2,2-dimethylcyclopropanecarboxamido)-2-heptenoic acid; Z-2-(2,2-dimethylcyclopropanecarboxamido)-5-phenyl-2-pentenoic acid; Z-2-(2,2-dimethylcyclopropanecarboxamido)-2-nonenoic acid; Z-2-(2,2-dimethylcyclopropanecarboxamido)-2-decanoic acid; Z-2-(2,2-dimethylcyclopropanecarboxamido)-2-tridecnoic acid; Z-2-(2,2-dimethylcyclopropanecarboxamido)-6-methoxy-2-hexenoic acid; Z-2-(2,2-dimethylcyclopropanecarboxamido)-6-methyl-2-heptenoic acid; Z-4-cyclohexyl-2-(2,-dimethylcyclopropanecarboxamido)-2-butenoic acid;

Z-2-cyclobutylacetamido-2-butenoic acid; Z-2-cyclopentylacetamido-2-butenoic acid; Z-2-cyclohexylacetamido-2-butenoic acid; Z-2-(4-cyclohexylbutyramido)-2-butenoic acid; Z-2-cyclopropylacetamido-2-butenoic acid; Z-2-cyclopropylacetamido-2-pentenoic acid; Z-2-(3-cyclopentylpropionamido)-2-butenoic acid; Z-2-(3-cyclohexylpropionamido)-2-butenoic acid; Z-2-(4-(2-thienyl)-butyramido)2-butenoic acid; Z-2-(4-phenylbutyramido)-2-butenoic acid, Z-2-(D,L-α-lipoamido)-2-pentenoic acid; Z-2-(D,L-α-lipoamido)-2-cinnamic acid; Z-2(3-(2-tetrahydrofuryl)-propionamido)-2-butenoic acid, or a sodium, potassium, ammonium calcium, magnesium or trimethylammonium salt thereof, or (2) a compound selected from Z-2-(2,2-dimethylcyclopropane carboxamido)-8-trimethyl ammonium-2-octenoic acid, Z-8-[(carboxymethyl)methylamino]-2-(2,2-diemthylcyclopropanecarboxamido)-2-octenoic acid.

Z-8-[(2-amino-2-oxoethyl)thio]-2-(2,2-dimethylcyclopropanecarboxamido)-2-octenoic acid.

Z-2-(2,2-dimethylcyclopropanecarboxamido)-8-[1-(phosphono)ethylamino-2-octenoic acid, Z-7-(L-amino-2-carboxyethylthio)-2-dimethyl-cyclopropanecarboxamido)-2-heptenoic acid.

Z-8-acetamido-2-(2,2-dimethylcyclopropanecarboxamido)-2-octenoic acid.

Z-7-(3-hydroxyl-2-pyridylthio)-2-(2,2-diemthylcyclopropanecarboxamido)-2-heptenoic acid, Z-(3-carboxyl-2-pyridylthio)-2-(2,2-dimethylcyclopropanecarboxamido)-2-heptenoic acid, or a sodium, potassium, ammonium, calcium, magnesium, or trimethylammonium salts thereof: to 1 part by weight of said antibiotic.

20. A method of preventing the nephrotoxic effect in animals of an antibiotic which is thienamycin, N-guanyl or N-formimidoyl thienamycin which comprises co-administering to the animal from about 0.1 to 3 parts by weight of a 3-substituted propenoic acid selected from Z-2-(2,2-dimethylcyclopropane carboxamido)-8-trimethyl ammonium-2-octenoic acid, Z-2-(2,2-dimethylcyclopropane carboxamido)-2-butenoic acid, Z-2-(2,2-dimethylcyclopropane carboxamido)-2-pentenoic acid, Z-2-(2,2-dimethylcyclopropanecarboxamido)-2-ocetonic acid, Z-2-(2,2-dimethylcyclopropane carboxamido)-2-hexenoic acid, Z-8-[(carboxymethyl)methylamino]-2-(2,2-dimethylcyclopropanecarboxamido)-2-octenoic acid, Z-8-[(2-amino-2-oxoethyl)thio]-2-(2,2-dimethylcyclopropanecarboxamido)-2-octenoic acid, Z-2-(2,2-dimethylcyclopropanecarboxamidd)-8-[1-(phosphono) ethylamino]-2-octenoic acid, Z-7-(L-amino-2-carboxyethyethylthio)-2-(2,2-dimethylcyclopropanecarboxamido)-2-heptenoic acid, Z-8-acetamido-2-(2,2-dimethylcyclopropanecarboxamido)-2-octenoic acid, or a sodium, potassium, calcium magnesium, ammonium or trimethylammonium salt thereof; to 1 part by weight of said antibiotic.

21. The method of claim 3 wherein said antibiotic is N-formimidoyl thienamycin and said 3-substituted propenoic acid is 2-7-(L-amino-2-carboxyethylthio)-2-(2,2-dimethylcyclopropanecarboxamido)-2-heptenoic acid.

* * * * *